United States Patent
Desai et al.

(10) Patent No.: US 7,951,400 B2
(45) Date of Patent: May 31, 2011

(54) COATED TABLET FORMULATION AND METHOD

(75) Inventors: Divyakant S. Desai, West Windsor, NJ (US); Bing V. Li, Germantown, MD (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1285 days.

(21) Appl. No.: 11/137,068

(22) Filed: May 25, 2005

(65) Prior Publication Data

US 2005/0266080 A1 Dec. 1, 2005

Related U.S. Application Data

(60) Provisional application No. 60/575,319, filed on May 28, 2004.

(51) Int. Cl.
*A61K 9/24* (2006.01)
*A61K 9/20* (2006.01)
*A61K 9/22* (2006.01)
*A61K 9/28* (2006.01)

(52) U.S. Cl. ........ 424/472; 424/464; 424/465; 424/468; 424/474

(58) Field of Classification Search .................. None
See application file for complete search history.

(56) References Cited

U.S. PATENT DOCUMENTS

| | | | |
|---|---|---|---|
| 4,800,084 A | 1/1989 | Zerbe | |
| 4,847,265 A | 7/1989 | Badorc et al. | |
| 5,158,777 A | 10/1992 | Abramowitz et al. | |
| 5,428,048 A | 6/1995 | Malamas et al. | |
| 5,489,436 A | 2/1996 | Hoy et al. | |
| 5,541,205 A | 7/1996 | Malamas et al. | |
| 5,849,911 A | 12/1998 | Fässler et al. | |
| 6,086,919 A | 7/2000 | Bauer et al. | |
| 6,087,383 A | 7/2000 | Singh et al. | |
| 6,136,345 A | 10/2000 | Grimmett et al. | |
| 6,316,438 B1 | 11/2001 | Yu et al. | |
| 6,395,767 B2 | 5/2002 | Robl et al. | |
| 6,414,002 B1 | 7/2002 | Cheng et al. | |
| 6,653,314 B2 | 11/2003 | Cheng et al. | |
| 6,670,344 B2 | 12/2003 | Venit et al. | |
| 6,727,271 B2 | 4/2004 | Cheng et al. | |
| 6,753,012 B2 | 6/2004 | Cappola | |
| 2002/0019411 A1 | 2/2002 | Robl et al. | |
| 2002/0094992 A1 | 7/2002 | MacLean | |
| 2004/0022855 A1 | 2/2004 | Yoon et al. | |
| 2005/0208133 A1 | 9/2005 | Tsutsumi et al. | |
| 2005/0214373 A1 | 9/2005 | Desai et al. | |
| 2005/0256202 A1 | 11/2005 | Kim et al. | |
| 2005/0256314 A1 | 11/2005 | Kim et al. | |
| 2005/0288343 A1 | 12/2005 | Rusowicz et al. | |

FOREIGN PATENT DOCUMENTS

| | | |
|---|---|---|
| EP | 0 177 355 | 7/1990 |
| EP | 1 186 293 | 3/2002 |
| EP | 1 243 266 | 9/2002 |
| WO | WO 99/05027 | 2/1999 |
| WO | WO 01/52825 | 7/2001 |
| WO | WO 02/085335 | 10/2002 |
| WO | WO 03/059330 | 7/2003 |
| WO | WO 2004/043912 | 5/2004 |

OTHER PUBLICATIONS

Abdel-Magid, A.F. et al., "Reductive Amination of Aldehydes and Ketones with Sodium Triacetoxyborohydride. Studies on Direct and Indirect Reductive Amination Procedures", J. Org. Chem., vol. 61, No. 11, pp. 3849-3862 (1996).
Bennett, A.E. et al., "Heteronuclear decoupling in rotating solids", J. Chem. Phys., vol. 103, No. 16, pp. 6951-6958 (1995).
Cosier, J. et al., "A Nitrogen-Gas-Stream Cryostat for General X-ray Diffraction Studies", J. Appl. Cryst., vol. 19, pp. 105-107 (1986).
U.S. Appl. No. 11/085,710, filed Mar. 21, 2005, Desai et al.
Earl, W.L. et al., "Measurement of $^{13}C$ Chemical Shifts in Solids", Journal of Magnetic Resonance, vol. 48, pp. 35-54 (1982).
Johannsson, G. et al., "Growth Hormone Treatment of Abdominally Obese Men Reduces Abdominal Fat Mass, Improves Glucose and Lipoprotein Metabolism, and Reduces Diastolic Blood Pressure", Journal of Clinical Endocrinology and Metabolism, vol. 82, No. 3, pp. 727-734 (1997).
Jones, A.G. et al., "Programmed Cooling Crystallization of Potassium Sulphate Solutions", Chemical Engineering Science, vol. 29, pp. 105-118 (1974).
Metz, G. et al., "Ramped-Amplitude Cross Polarization in Magic-Angle-Spinning NMR", Journal of Magnetic Resonance, Series A, vol. 110, pp. 219-227 (1994).
Mullin, J.W. et al., "Programmed cooling of batch crystallizers", Chemical Engineering Science, vol. 26, pp. 369-377 (1971).
Otwinowski, Z. et al., "Processing of X-Ray Diffraction Data Collected in Oscillation Mode", Macromolecular Crystallography, Part A, Methods in Enzymology, vol. 276, Academic Press, publ., Carter, Jr., C.W. et al., eds., pp. 307-326 (1997).

(Continued)

*Primary Examiner* — Humera N Sheikh
(74) *Attorney, Agent, or Firm* — McDonnell Boehnen Hulbert & Berghoff LLP

(57) ABSTRACT

A coated tablet formulation is provided which includes a medicament such as the DPP4-inhibitor, saxaglipitin

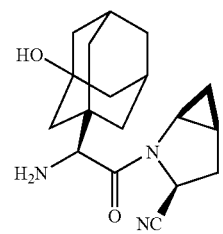

or its HCl salt,
which is subject to intra-molecular cyclization, which formulation includes a tablet core containing one or more fillers, and other conventional excipients, which tablet core includes a coating thereon which may include two or more layers, at least one layer of which is an inner seal coat layer which is formed of one or more coating polymers, a second layer of which is formed of medicament which is the DPP4-inhibitor and one or more coating polymers, and an optional, but preferable third outer protective layer which is formed of one or more coating polymers. A method for forming the coated tablet is also provided.

10 Claims, No Drawings

OTHER PUBLICATIONS

Xu, Z. et al., "Process Research and Development for an Efficient Synthesis of the HIV Protease Inhibitor BMS-232632", Organic Process Research & Development, vol. 6, No. 3, pp. 323-328 (2002).

Yin, S. et al., "Simulated PXRD Patterns in Studies of the Phase Composition and Thermal Behavior of Bulk Crystalline Solids", American Pharmaceutical Review, vol. 6, No. 2, pp. 80-85 (2003).

Goldstein, S.W. et al., "Hydroxyurea Derivatives as Hypoglycemic Agents", J. Med. Chem., vol. 36, No. 15, pp. 2238-2240 (1993).

Malamas, M.S. et al., "Azole Phenoxy Hydroxyureas as Selective and Orally Active Inhibitors of 5-Lipoxygenase", J. Med. Chem., vol. 39, No. 1, pp. 237-245 (1996).

Edwin B. Villhauer et al., "1-[[(3-Hydroxy-1-adamantyl)amino]acetyl]-2-cyano-(s)-pyrrolidine: A Potent, Selective, and Orally Bioavailable Dipeptidyl Peptidase IV Inhibitor with Antihyperglycemic Properties," J. Med. Chem., 2003, pp. 2774-2789, vol. 46.

COATED TABLET FORMULATION AND METHOD

This application claims a benefit of priority from U.S. Provisional Application No. 60/575,319, filed May 28, 2004, the entire disclosure of which is herein incorporated by reference.

FIELD OF THE INVENTION

The present invention relates to a coated tablet formulation which includes a tablet core coated with a medicament such as a DPP4-inhibitor, such as saxagliptin, and to a method for preparing such coated tablet formulation.

BACKGROUND OF THE INVENTION

The compound of the structure

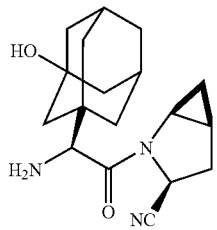

or its HCl salt, (hereinafter the above DPP4-inhibitor or saxaglipitin) is an orally active reversible dipeptidyl peptidase-4 (DPP4) inhibitor, which is a therapeutic agent for treatment of Type-2 diabetes mellitus which is disclosed in U.S. Pat. No. 6,395,767.

After a meal intake, insulinotropic hormone GLP-1 is released which in turn induces insulin release from the pancreas. Some of the GLP-1 is inactivated by the DPP4 present in plasma and intestinal capillary endothelium. Therefore, if the DPP4 is inhibited, more GLP-1 will be available to activate insulin release from the pancreas. The advantage of this mechanism of insulin release is that insulin is secreted only in response to a meal. Therefore, problems of hypoglycemia associated with other diabetes drugs will be less likely with a DPP4 inhibitor.

The above DPP4 inhibitor is a labile compound which is prone to an intra-molecular cyclization as shown below.

Formation of Cyclic Amidine (CA)

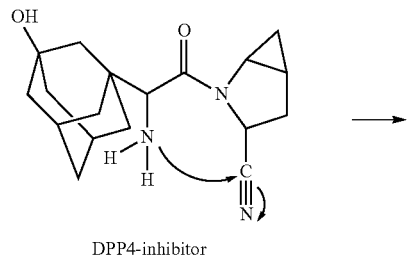

DPP4-inhibitor

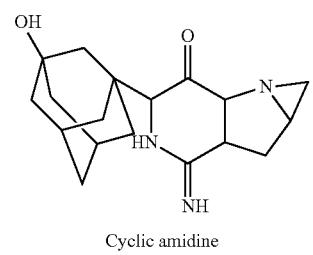

Cyclic amidine

The resultant degradant, cyclic amidine (mainly cis-cyclic amidine (CA)), is not therapeutically active and therefore, its formation is not desirable. This cyclization reaction can occur both in solid state and solution state. The rate of intra-molecular cyclization is accelerated when formulations are subject to commonly used processing activities such as wet granulation, roller compaction, or tabletting. In addition, most commonly used excipients, when mixed with this compound, can accelerate the rate of cyclization. Moreover, the level of cis-cyclic amidine increases when the drug to excipient ratio increases posing more challenges for low strength dosage forms. Given these properties of the molecule, manufacture of a conventional tablet dosage form for the DPP4-inhibitor, which is a preferred dosage form, is not a viable option.

Currently, capsule formulations containing a dry mix of the DPP4-inhibitor and commonly used excipients are manufactured at a small scale and used for clinical studies. The scale up of capsule formulations containing the DPP4-inhibitor will also be problematic since it will involve milling to control the particle size of the DPP4-inhibitor so that capsules of lower strengths are manufactured without content uniformity problems.

Additionally, most of the therapeutic agents as a single entity or as a combination product for diabetes treatments are available in a tablet dosage form. Since a tablet dosage form using traditional manufacturing process is not feasible for the DPP4-inhibitor, its manufacturing with other therapeutic agents, as a combination tablet will be even more problematic.

Thus, it is seen that there is clearly a need for stable pharmaceutical formulations containing medicaments which are subject to intra-molecular cyclization which results in formation of degradants such as cyclic amidines which are not therapeutically active.

U.S. Pat. No. 6,395,767 to Robl et al. (hereinafter Robl et al.) discloses cyclopropyl-fused pyrrolidine-based dipeptidyl peptidase IV inhibitors (DPP4 inhibitors) which include compounds having the structure

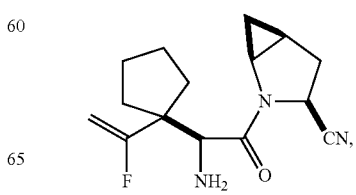

-continued

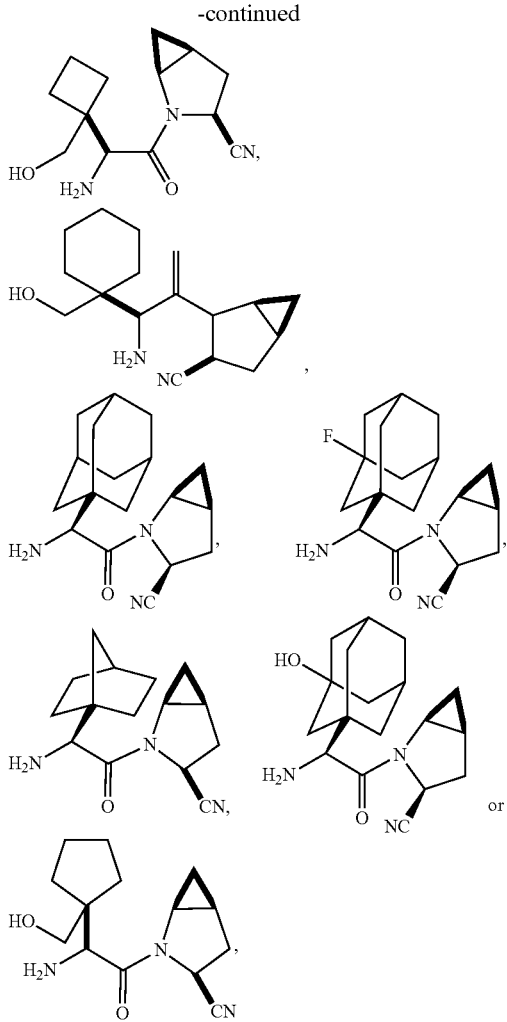

or a pharmaceutically acceptable salt thereof, wherein the pharmaceutically acceptable salt can be the hydrochloride salt or the trifluoroacetic acid salt.

Robl et al. discloses that the DPP4 inhibitors including those set out above may be formulated as tablets, capsules, granules or powders.

BRIEF DESCRIPTION OF THE INVENTION

In accordance with the present invention a coated tablet is provided which may include a medicament which is subject to intra-molecular cyclization, but is surprisingly stable under normal storage conditions, that is at 30° C. and 60% relative humidity.

The coated tablet of the invention includes a tablet core (also referred to as a "core", "tablet core", "placebo", "placebo core tablet", "tablet core composition" or "core composition") and a) a coating layer coated on the core, which coating layer is an inner seal coat formed of at least one coating polymer;
b) a second coating layer, disposed over the inner seal coat, formed of a medicament and at least one coating polymer which preferably is the same coating polymer in the inner seal coat; and optionally
c) an outer protective coating layer, disposed over the second coating layer, formed of at least one coating polymer, which preferably is the same coating polymer in the second coating layer and inner seal coat, but need not necessarily include the same amounts of such polymer.

The medicament will preferably be the DPP4-inhibitor of the structure

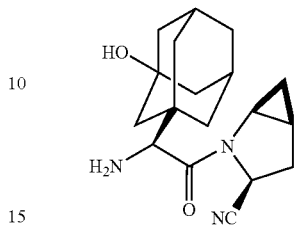

A or a pharmaceutically acceptable salt thereof, such as the HCl salt, also referred to as Compound A.

In a preferred embodiment, the coated tablet of the invention will include a tablet core which is formed of one or more bulking agents or fillers, optionally one or more binders, optionally one or more disintegrants, and optionally one or more tableting lubricants, a) an inner seal coating layer which includes at least one coating polymer which preferably is a polyvinyl alcohol (PVA) based polymer;
b) a second coating layer disposed over the seal coating layer a) which includes at least one medicament and at least one coating polymer which is preferably a PVA based polymer, and preferably the same as the coating polymer of the inner seal coating layer.

The above coating layers are applied to the tablet core preferably by spray coating on to the tablet core.

In a more preferred embodiment of the invention, an outer protective or third coating layer will be coated over the second coating layer (containing the medicament) and will function as a protective layer. The third or protective coating layer may preferably include similar components as in the second coating layer except that it will not include a medicament, but may optionally include one or more colorants, and may not necessarily include the same amounts of such components. Optionally, a fourth layer (which includes similar components as in the third layer) containing colorants and a coating polymer can also be applied to differentiate tablets of various strengths. The first, second, third and fourth coating layers may be formed of the same or different coating polymers.

It has been found that the coated tablets of the invention exhibit superior chemical stability as compared to traditional tablets manufactured using conventional dry granulation or wet granulation techniques.

The coating approach will also facilitate preparation of a combination formulation of a problematic medicament with another drug by using the other drug tablet as a starting tablet (instead of the tablet core or placebo mentioned above) and applying the inner seal coating and the second coating containing the problematic medicament and coating polymer, and optionally but preferably, the outer protective coating over the other drug tablet.

The coated tablets of the invention may be prepared preferably using perforated pan coaters. Fluid bed coating and spray coating may be used as well.

In addition, in accordance with the present invention, a method is provided for preparing the coated tablet of the invention, which method includes the steps of a) providing a tablet core;
b) coating the tablet with an inner seal coating layer formulation which includes at least one coating polymer;

c) drying the coated tablet to form an inner seal coating thereon;

d) coating the so-coated tablet with a second coating layer formulation which includes medicament and at least one coating polymer;

e) drying the so-coated tablet to form a second coating layer (containing medicament) thereon;

f) optionally, but preferably, coating the so-coated tablet with a third outer protective coating layer formulation which includes at least one coating polymer; and g) optionally, coating the so-coated tablet with a fourth outer protective coating layer which includes at least one coating polymer and colorant, and h) drying the so-coated tablet to form the coated tablet of the invention.

In a preferred embodiment of the method of the invention the inner seal coating layer formulation, the second coating layer formulation and the outer protective coating layer(s) formulation(s) each will be applied as a suspension of the coating polymer in a coating solvent.

The third and fourth outer protective coating layers need not include a medicament (although it may, if desired), and may be formed of the other components of the first coating layer and/or second coating layer. The second coating layer may be formed of the components of the first coating layer and/or third/and or fourth coating layer, but not necessarily the same amounts of such components.

In preparing the coated tablet of the invention, coating suspensions which include coating polymer in water are prepared. Other coating solvents which may be employed include ethanol, methanol, and isopropyl alcohol, with water being preferred. Tablets which are placebos (contain no medicament) and form tablet cores are coated with the inner seal coating suspension and are dried. The second coating layer suspension containing medicament and coating polymer is applied over the so-coated tablets which are then dried.

Where the coated tablet of the invention is to include an outer protective layer, a coating suspension is prepared as in the case of the inner seal coating suspension but without medicament. The coating suspension will then be coated onto the previously coated tablets as described for the inner seal coating and second coating to form a protective coating layer thereon.

The coated tablets of the invention are useful in the treatment of mammals such as humans, dogs and cats for Type II diabetes.

DETAILED DESCRIPTION OF THE INVENTION

The tablet core or placebo employed in the coated tablet of the invention will include conventional pharmaceutical excipients to enable formation of a pharmaceutically acceptable solid tablet core. The tablet core may be in the form of a tablet, bead, beadlet, or pill, all of the above being collectively referred to as a tablet core.

The coated tablet of the invention will contain medicament, such as the above DPP4-inhibitor, saxaglipitin, in an amount within the range from about 0.1 to about 70% by weight and preferably from about 1 to about 50% by weight of the tablet core.

The tablet core employed in the coated tablet of the invention will preferably contain
a) at least one bulking agent or filler;
b) optionally at least one binder;
c) optionally at least one disintegrant; and
d) preferably but optionally at least one lubricant.

wherein
a) the bulking agent or filler is present in an amount within the range from about 1 to about 95% by weight, preferably from about 10 to about 85% by weight;
b) the binder is present in an amount within the range from about 0 to about 20% by weight, preferably from about 1 to about 10% by weight;
c) the disintegrant is present in an amount within the range from about 0 to about 20% by weight, and preferably from about 0.25 to about 10% by weight; and
d) the lubricant is present in an amount within the range from about 0 to about 5% by weight, preferably from about 0.2 to about 2% by weight, all of the above % by weight being based on the weight of the tablet core.

It is preferred that the bulking agents are microcrystalline cellulose and lactose monohydrate;
the disintegrant is croscarmellose sodium; and
the lubricant is magnesium stearate.

The tablet cores present in the coated tablets of this invention can be prepared by a variety of processes and order of addition of excipients. The utility of these formulations is not limited to a specific dosage form or manufacturing process. Tablet cores may be manufactured by wet granulation, dry granulation, direct blending or any other pharmaceutically acceptable process.

In accordance with the present invention, a preferred method is provided for preparing the tablet cores employed in the coated tablets of the invention which includes the steps of blending the one or more excipients such as bulking agent, optionally binder and optionally disintegrant. A lubricant will be preferably added to the blend to facilitate tablet formation.

The bulking agents or fillers will be present in the tablet core compositions of the invention in an amount within the range from about 1 to about 95% by weight and preferably from about 10 to about 85% by weight of the core composition. Examples of bulking agents or fillers suitable for use herein include, but are not limited to, cellulose derivatives such as microcrystalline cellulose or wood cellulose, lactose, sucrose, starch, pregelatinized starch, dextrose, mannitol, fructose, xylitol, sorbitol, corn starch, modified corn starch, inorganic salts such as calcium carbonate, calcium phosphate, dicalcium phosphate, calcium sulfate, dextrin/dextrates, maltodextrin, compressible sugars, and other known bulking agents or fillers, and/or mixtures of two or more thereof, preferably microcrystalline cellulose.

The binder will be optionally present in the pharmaceutical compositions of the invention in an amount within the range from about 0 to about 20% weight, preferably from about 1 to about 10% by weight of the core composition. Examples of binders suitable for use herein include, but are not limited to, hydroxypropyl cellulose, corn starch, pregelatinized starch, modified corn starch, polyvinyl pyrrolidone (PVP) (molecular weight ranging from about 5,000 to about 1,000,000, preferably about 40,000), hydroxypropyl methylcellulose (HPMC), lactose, gum acacia, ethyl cellulose, cellulose acetate, as well as a wax binder such as carnauba wax, paraffin, spermaceti, polyethylenes or microcrystalline wax, as well as other conventional binding agent and/or mixtures by two or more thereof, preferably hydroxypropyl cellulose.

The disintegrant will be optionally present in the pharmaceutical composition of the invention in an amount within the range from about 0 to about 20% by weight, preferably from about 0.25 to about 10% by weight of the core composition. Examples of disintegrants suitable for use herein include, but are not limited to, croscarmellose sodium, crospovidone, starch, potato starch, pregelatinized starch, corn starch, sodium starch glycolate, microcrystalline cellulose, low substituted hydroxypropyl cellulose or other known disintegrant, preferably croscarmellose sodium.

The lubricant will be optimally present in the pharmaceutical composition of the invention in an amount within the range from about 0.1 to about 5% by weight, preferably from about 0.2 to about 2% by weight of the core composition. Examples of tableting lubricants suitable for use herein include, but are not limited to, magnesium stearate, zinc stearate, calcium stearate, talc, carnauba wax, stearic acid, palmitic acid, sodium stearyl fumarate or hydrogenated vegetable oils and fats, or other known tableting lubricants, and/or mixtures of two or more thereof, preferably magnesium stearate.

The inner seal coating layer formulation (also referred to as the first coating layer) will include up to 95% of polymer based on the weight of the inner seal coating layer, and may be prepared as described hereinbefore. The formulation will contain at least one coating layer polymer and a coating solvent as described above, which preferably is water, which is used for processing and removed by drying. The coating layer polymer may be hydroxypropyl methylcellulose, polyvinyl alcohol (PVA), ethyl cellulose, methacrylic polymers or hydroxypropyl cellulose, preferably PVA. The coating layer may also optionally include a plasticizer such as triacetin, diethyl phthalate, tributyl sebacate or polyethylene glycol (PEG), preferably PEG; and an anti-adherent or glidant such as talc, fumed silica or magnesium stearate, opacifying agent such as titanium dioxide. The coating layer may also include iron oxide based colorants. The coating material is commercially available under the trade name Opadry® HP or Opadry® II white.

The second coating layer formulation will preferably be similar in composition to the first coating layer formulation although it will include medicament, preferably the DPP4-inhibitor in an amount within the range from about 0.5 to about 70%, preferably from about 30 to about 50% by weight, based on the weight of the second coating layer.

The third outer protective coating layer will preferably be similar in composition to the first coating layer.

The fourth coating layer where present will preferably be similar in composition to the third outer protective coating layer and will include colorant as desired, such as within the range from about 0.5 to about 5.0% by weight, based on the weight of the fourth coating layer.

The inner seal coating layer will preferably be formed of coating layer polymer in an amount within the range from about 10 to about 95%, preferably from about 20 to about 90% by weight of the inner seal coating layer, optionally plasticizer in an amount within the range from about 10 to about 30%, preferably from about 15 to about 20% by weight of the coating layer, and anti-adherent or glidant in an amount within the range for about 15 to about 30%, preferably from about 10 to about 15% by weight of the inner seal coating layer.

The second coating layer will be preferably formed of coating layer polymer in an amount within the range from about 30 to about 99.5%, preferably from about 40 to about 60% by weight of the second coating layer and medicament in an amount within the range from about 0.25% to about 70%, preferably from about 20 to about 50% by weight of the second coating layer.

The coating layer polymer in the second coating layer will be at least about 5 mg with a 200 mg tablet core, and the medicament will be at least about 0.5 mg.

The third outer protective coating layer will preferably be of similar composition to the first coating layer.

The inner seal coating layer will be present in an amount within the range from about 1 to about 5%, preferably from about 1 to about 3% by weight of the finished coated tablet; the second coating layer (containing medicament) will be present in an amount within the range from about 0.25 to about 70%, preferably from about 1 to about 50% by weight of the finished coated tablet, depending on potency; and the third outer protective coating layer and fourth layer where present will each be present in an amount within the range from about 1 to about 10%, preferably from about 1 to about 5% by weight of the finished coated tablet.

Preferred coated tablet formulations in accordance with the invention are set out below.

| Material<br>Tablet Placebo | Possible Range<br>%/mg by weight of 200 mg<br>placebo core tablet | Preferred Range<br>%/mg by weight of 200 mg<br>placebo core tablet |
|---|---|---|
| Bulking Agent | 2 to 95%/4 to 190 mg | 10 to 85%/20 to 170 mg |
| Lactose | 0 to 95%/0 to 190 mg | 20 to 75%/40 to 150 mg |
| Microcrystalline cellulose | 0 to 95%/0 to 190 mg | 20 to 75%/40 to 150 mg |
| Disintegrant | 0 to 20%/0 to 40 mg | 0.25 to 10%/0.5 to 20 mg |
| Croscarmellose sodium | 0 to 20%/0 to 40 mg | 2 to 10%/4 to 20 mg |
| Lubricant | 0.1 to 5%/0.2 to 10 mg | 0.2 to 2%/0.4 to 4 mg |
| Magnesium Stearate | 0.1 to 5%/0.2 to 10 mg | 0.2 to 2%/0.4 to 4 mg |

| First Inner Seal Coating Layer | %/mg by weight of 200 mg<br>placebo core tablet | %/mg by weight of 200 mg<br>placebo core tablet |
|---|---|---|
| Coating polymer, and optional plasticizer and glidants | 0.5 to 50%/1 to 100 mg | 1 to 3%/2 to 6 mg |

| Second Coating Layer | %/mg by weight of 200 mg<br>placebo core tablet | %/mg by weight of 200 mg<br>placebo core tablet |
|---|---|---|
| DPP4-inhibitor (free base or HCl salt) | 0.1 to 70%/0.2 to 140 mg | 1 to 50%/2 to 100 mg |
| Coating polymer, and optional plasticizer and glidants | 1 to 70%/2 to 140 mg | 1 to 50%/2 to 100 mg |

| Third Outer Protective Coating Layer | %/mg by weight of 200 mg placebo core tablet | %/mg by weight of 200 mg placebo core tablet |
|---|---|---|
| Coating polymer, and optional plasticizer, glidants and color | 0.5 to 50%/1 to 100 mg | 1 to 5%/2 to 10 mg |

The following working Example represents a preferred embodiment of the invention.

Example

A 500 g batch of 2.5 mg DPP4 coated tablets having the following composition were prepared as described below

| Tablet Core | Weight (mg) % by weight of a 200 mg placebo core tablet |
|---|---|
| Lactose Monohydrate NF | 99 mg (49.5%) |
| Microcrystalline Cellulose NF | 90 mg (45%) |
| Croscarmellose Sodium NF | 10 mg (5%) |
| Magnesium Stearate NF | 1 mg (0.5%) |
| Total | 200 mg (100.0%) |
| Inner Seal Coating Layer Opadry ® HP which contains the following ingredients | 4 mg (2%) |
| Polyvinyl Alcohol 40% PEG 20% Talc 15% Titanium dioxide 25% Middle Layer | |
| DPP4-inhibitor, Saxaglipitin | 2.5 mg (1.25%) |
| Opadry ® HP | 20 mg (10%) |
| Outer Protective Layer | |
| Opadry ® HP | 4 mg (2%) |

The 500 g of tablet cores were prepared as follows.

Lactose monohydrate, croscarmellose sodium, and microcrystalline cellulose were blended in a planetary mixer. The blend was then lubricated by blending with pre-screened magnesium stearate using a Turbula mixer. The lubricated blend was compressed using a single station press or using a rotary press into 200 mg placebo tablets.

Inner Seal Coating Layer

The inner seal coating suspension was prepared as follows.

0.1 N HCl (about 226.7 g) in a metal container was continuously stirred with a lightening mixer. 40 g Opadry® HP powder was quickly added into the vortex. After the powder addition was completed, mixing was continued at a low speed until a uniform mixture was visually evident. pH of the resulting suspension was measured and pH was adjusted to 2 using concentrated HCl or NaOH.

A Glatt coater was set up according to the following parameters

| Glatt Coater Parameter | |
|---|---|
| Pump rate | 3.5-5 ml/min |
| Pan speed | 20 rpm |
| Air pressure | 1.5 bar |
| Inlet air temperature | 50° C. |
| Exhaust air temperature | about 38° C. |
| Air flow | 80 m³/hour |

| Glatt Coater Parameter | |
|---|---|
| Gun to bed distance | 6.5 inch |
| Nozzle size | 0.8 mm |

The tablet cores were preheated in a coating pan for about 10 to 15 minutes. 30 heated tablets were weighed. Drying of the tablets was continued until the moisture was driven out of the tablet and tablet weight became constant. The final weight of 30 tablets was designed as A.

The 30 tablets were coated with the inner seal coating suspension as prepared above employing the Glatt coater.

The 30 tablets were weighed every 10 minutes (and the weight recorded) until the tablet weight reached the targeted weight (Equation 1). The coated tablets were dried by heating until the tablet weight became constant. The final weight of the so-coated tablets was designated as B.

$$\text{Targeted weight} = A \times 1.02 = B \quad \text{Equation 1}$$

Middle (Drug) Coating Layer

The middle drug-containing coating layer suspension was prepared as follows.

12.5 g of the DPP4-inhibitor (free base) was added to 1000 ml of 0.1 N HCl in a metal container. The pH was measured and adjusted to 2. The HCl was continuously stirred and 100 g Opadry® HP was quickly added into the vortex. The mixture was then stirred at low speed until a uniform mixture was visually evident. The pH of the suspension was maintained at 2 using either concentrated HCl or 1N HCl as necessary.

The seal coated tablet cores prepared above were coated with the coating suspension containing the DPP4-inhibitor prepared above employing the Glatt coater. The 30 seal coated tablets were weighed, initially every 30 minutes, then every 15 minutes and the weight recorded until the targeted weight was reached (Equation 2). The so-coated tablets were dried by heating until the tablet weight became constant. The final weight of 30 tablets was designated as C.

$$\text{Targeted weight} = B + 30 \times (2.925 \text{(equivalent to 2.5 mg free base)} + 20 \text{ mg}) = B + 687.75 \text{ mg} = C \quad \text{Equation 2}$$

The amount of drug coated onto the tablets was determined using HPLC, fiber optic probe, or NIR or other suitable means. Coating was stopped when the targeted amount of drug was deposited.

Outer Protective Coating Layer

The so-coated tablets were then coated with a suspension of Opadry® HP as used in forming the inner seal coating. The 30 tablets were weighed every 10 minutes and the weight recorded until tablet weight reached the targeted weight (Equation 3). The tablets were dried by heating until the tablet weight became constant.

The final weight of 30 tablets was designed as D.

$$\text{Targeted weight} = C + 30 \times 4 \text{ mg} = C + 120 \text{ mg} = D \quad \text{Equation 3}$$

The so-coated tablets were transferred to a suitable container.

The tablets of the invention so-prepared had superior stability to conventional tablet formulations (wherein the drug was in the core) and capsule formulations.

The above 2.5 mg potency coated tablets of the invention were stored at various storage conditions up to and including 41 weeks and stability data related to presence of the degradant cyclic amidine (mainly cis-cyclic amidine (Cis-CA)) were collected. As shown in Table 1 set out below, no cis-CA was detected at 25° C./60% RH storage condition. The cis-CA levels were 0.22% and 0.32% at 30° C./60% RH and 40° C./75% RH storage conditions, respectively. These levels are significantly lower than those observed in the 5 mg and 20 mg potency capsule formulations shown in Table 2.

TABLE 1

Twenty-six weeks stability data on 2.5 mg potency tablets coated with Opadry ® HP, free base as starting material, and three coating layers. For stability evaluation, tablets were packaged in HDPE bottles.

| Storage Condition | 2 wks for all closed conditions | | | 4 wks for all closed conditions 1 wk for two open conditions | | | 8 wks for all closed conditions 5 wks for two open conditions | | |
|---|---|---|---|---|---|---|---|---|---|
| | Amide % | Cis-CA % | Trans-CA % | Amide % | Cis-CA % | Trans-CA % | Amide % | Cis-CA % | Trans-CA % |
| 5° C.-closed | 0 | 0 | 0 | 0 | 0 | 0 | 0 | 0 | 0 |
| 25° C./60% RH-closed | 0 | 0 | 0 | 0 | 0 | 0 | 0 | 0 | 0 |
| 30° C./60% RH-closed | 0 | 0 | 0 | 0 | 0 | 0 | 0 | 0 | 0 |
| 40° C./75% RH-closed | 0 | 0 | 0 | 0 | 0.05 | 0 | 0 | 0.09 | 0 |
| 50° C.-closed | 0 | 0.17 | 0 | 0 | 0.33 | 0.15 | 0 | 0.52 | 0.12 |
| 30° C./60% RH-open | NA | NA | NA | 0 | 0 | 0 | 0 | 0.20 | 0.06 |
| 40° C./75% RH-open | NA | NA | NA | 0 | 0.68 | 0.15 | 0 | 3.22 | 0.42 |

| Storage Condition | 12 wks for all closed conditions | | | 26 wks for all closed conditions | | | 41 wks for all closed conditions | | |
|---|---|---|---|---|---|---|---|---|---|
| | Amide % | Cis-CA % | Trans-CA % | Amide % | Cis-CA % | Trans-CA % | Amide % | Cis-CA % | Trans-CA % |
| 5° C.-closed | 0 | 0 | 0 | 0 | 0 | 0 | 0 | 0 | 0 |
| 25° C./60% RH-closed | 0 | 0 | 0 | 0 | 0 | 0 | 0.03 | 0 | 0 |
| 30° C./60% RH-closed | 0 | 0 | 0 | 0 | 0.22 | 0 | 0.03 | 0.17 | 0 |
| 40° C./75% RH-closed | 0 | 0.20 | 0.05 | 0 | 0.32 | 0 | 0.03 | 0.90 | 0 |
| 50° C.-closed | 0 | 0.75 | 0.15 | 0 | 1.00 | 0 | 0 | 1.62 | 0 |
| 30° C./60% RH-open | NA | NA | NA | NA | NA | NA | NA | NA | NA |
| 40° C./75% RH-open | NA | NA | NA | NA | NA | NA | NA | NA | NA |

NA denotes "data not available"

TABLE 2

Stability data for capsule formulations (benzoate salt of DPP4 4.8%, Anhydrous lactose 50.2%, lactose hydrous 40%, croscarmellose sodium 2%, and sodium stearyl fumarate 3%, fill weights for 5 mg and 20 mg capsules are 150 mg and 350 mg, respectively.)

| | 5 mg capsule | | | | 20 mg capsule | | | |
|---|---|---|---|---|---|---|---|---|
| Conditions | 2 wks Cis-CA % | 4 wks Cis-CA % | 13 wks Cis-CA % | 26 wks Cis-CA % | 2 wks Cis-CA % | 4 wks Cis-CA % | 13 wks Cis-CA % | 26 wks Cis-CA % |
| 25° C./60% RH-closed | 0.11 | 0.13 | 0.20 | 0.31 | 0.08 | 0.05 | 0.14 | 0.26 |
| 40° C./75% RH-closed | 0.23 | 0.35 | 0.61 | 0.95 | 0.22 | 0.26 | 0.46 | 0.62 |
| 50° C.-closed | NA | 0.73 | 1.72 | NA | NA | 0.43 | 1.19 | NA |

What is claimed is:

1. A coated tablet comprising
   (a) a tablet core;
   (b) an inner seal coating layer coated on the tablet core wherein the inner seal coating layer comprises about 1 mg to about 100 mgs of a polyvinyl alcohol based formulation wherein the polyvinyl alcohol based formulation comprises polyvinyl alcohol;
   (c) a second coating layer coated on the inner seal coating of the tablet core, wherein the second coating layer comprises about 0.2 mgs to about 140 mgs of saxagliptin, or a pharmaceutically acceptable salt thereof, and about 2 mgs to about 140 mgs of a polyvinyl alcohol based formulation wherein the polyvinyl alcohol based formulation comprises polyvinyl alcohol; and
   (d) an outer protective coating layer coated on the second coating layer of the tablet core wherein the outer protective coating layer comprises about 1 mg to about 100 mgs of a polyvinyl alcohol based formulation wherein the polyvinyl alcohol based formulation comprises polyvinyl alcohol.

2. The coated tablet as defined in claim 1 wherein the tablet core is comprised of one or more fillers, optionally one or more binders, optionally one or more disintegrants and optionally one or more tableting lubricants.

3. The coated tablet as defined in claim 2 wherein the tablet core is comprised of microcrystalline cellulose, lactose monohydrate, croscarmellose sodium, and magnesium stearate.

4. The coated tablet as defined in claim 1 having the following composition:

| Tablet Core | Range % by weight for 200 mg tablet core |
|---|---|
| Lactose | 20 to 75%/40 to 150 mg |
| Microcrystalline cellulose | 20 to 75%/40 to 150 mg |
| Croscarmellose sodium | 2 to 10%/4 to 20 mg |
| Magnesium Stearate | 0.2 to 2%/0.4 to 4 mg |

| Inner Seal Coating Layer | % by weight of 200 mg tablet core |
|---|---|
| Polyvinyl Alcohol Based Formulation and optional plazticizer and glidants | 1 to 3%/2 to 6 mg |

| Second Coating Layer | % by weight of 200 mg tablet core |
|---|---|
| Polyvinyl Alcohol Based Formulation and optional plazticizer and glidants | 0.25 to 70%/0.5 to 140 mg<br>1 to 50%/2 to 100 mg |

| Outer Protective Coating Layer | % by weight of 200 mg tablet core |
|---|---|
| Polyvinyl Alcohol Based Formulation and optional plazticizer, glidants and color. | 1 to 5%/2 to 10 mg |

5. The coated tablet as defined in claim 1 where for a 5 mg potency the second coating layer is comprised of 5 mg saxagliptin, and at least 5 mg polyvinyl alcohol based formulation and for a 2.5 mg potency the second coating layer is comprised of 2.5 mg saxagliptin, and 20 mg polyvinyl alcohol based formulation.

6. A coated tablet comprising:
a) a tablet core comprising about 49.5% lactose monohydrate, about 45% microcrystalline cellulose, about 5% croscarmellose sodium, and about 0.5% magnesium stearate;
b) an inner seal coating layer coated on the tablet core, wherein the inner seal coating layer comprises about 40% polyvinyl alcohol, about 20% polyethylene glycol, about 15% talc, and about 25% titanium dioxide;
c) a second coating layer coated on the inner seal coating of the tablet core, wherein the second coating layer comprises saxagliptin or a pharmaceutically acceptable salt thereof, polyvinyl alcohol, polyethylene glycol, talc, and titanium dioxide; and
d) optionally an outer protective coating layer coated on the second coating layer of the tablet core, wherein the outer protective coating comprises polyvinyl alcohol, polyethylene glycol, talc, and titanium dioxide.

7. The coated tablet as defined in claim 6 wherein the second coating layer comprises saxagliptin or a pharmaceutically acceptable salt thereof, and a coating material comprising about 40% polyvinyl alcohol, about 20% polyethylene glycol, about 15% talc, and about 25% titanium dioxide.

8. The coated tablet as defined in claim 7 wherein the outer protective coating layer comprises about 40% polyvinyl alcohol, about 20% polyethylene glycol, about 15% talc, and about 25% titanium dioxide.

9. The coated tablet as defined in claim 8 wherein saxagliptin is the hydrochloride salt.

10. The coated tablet as defined in claim 1 wherein saxagliptin is the hydrochloride salt.

* * * * *

UNITED STATES PATENT AND TRADEMARK OFFICE
CERTIFICATE OF CORRECTION

PATENT NO. : 7,951,400 B2
APPLICATION NO. : 11/137068
DATED : May 31, 2011
INVENTOR(S) : Desai et al.

It is certified that error appears in the above-identified patent and that said Letters Patent is hereby corrected as shown below:

On the Title Page

Item (57) in the Abstract, at Column 2, Line 2, "saxaglipitin" should be replaced with "saxagliptin".

In the Claims

In Claim 4, at Column 13, Line 23 (approximately), "plazticizer" should be replaced with "plasticizer".

In Claim 4, at Column 13, Line 39 (approximately), "plazticizer" should be replaced with "plasticizer".

In Claim 4, at Column 13, Lines 27-31 (approximately), the table text

" 
| Second Coating Layer | % by weight of 200 mg tablet core |
|---|---|
| Polyvinyl Alcohol Based Formulation and optional plazticizer and glidants | 0.25 to 70%/0.5 to 140 mg<br>1 to 50%/2 to 100 mg |

"

should be replaced with

"
| Second Coating Layer | % by weight of 200 mg tablet core |
|---|---|
| saxagliptin (free base or HCl salt) | 0.25 to 70%/0.5 to 140 mg |
| Polyvinyl Alcohol Based Formulation and optional plasticizer and glidants | 1 to 50%/2 to 100 mg |

".

Signed and Sealed this
Thirteenth Day of May, 2014

Michelle K. Lee
*Deputy Director of the United States Patent and Trademark Office*